United States Patent
Shimura

(10) Patent No.: US 7,374,077 B2
(45) Date of Patent: May 20, 2008

(54) SIMILAR IMAGE SEARCH SYSTEM

(75) Inventor: Kazuo Shimura, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 10/405,036

(22) Filed: Apr. 2, 2003

(65) Prior Publication Data
US 2004/0003001 A1    Jan. 1, 2004

(30) Foreign Application Priority Data
Apr. 3, 2002  (JP) ............................ 2002-100776
Oct. 22, 2002 (JP) ............................ 2002-307070

(51) Int. Cl.
*G06F 17/00* (2006.01)

(52) U.S. Cl. ...................... 235/375; 382/209; 382/218; 382/219

(58) Field of Classification Search ................ 235/385, 235/375, 383, 462.41; 705/22, 28; 378/62, 378/65; 382/115–18, 128–132, 181, 209, 382/214, 218–219; 600/437, 425, 300, 443
See application file for complete search history.

(56) References Cited

U.S. PATENT DOCUMENTS

| | | | |
|---|---|---|---|
| 5,172,418 A * | 12/1992 | Ito et al. ...................... 382/132 |
| 5,224,036 A * | 6/1993 | Ito et al. ...................... 382/132 |
| 5,482,029 A * | 1/1996 | Sekiguchi et al. ........... 600/109 |
| 5,528,492 A * | 6/1996 | Fukushima .................... 707/1 |
| 5,697,368 A * | 12/1997 | Luber et al. ................ 600/407 |
| 5,732,121 A | 3/1998 | Takeo et al. |
| 5,807,256 A * | 9/1998 | Taguchi et al. ............. 600/425 |
| 5,813,984 A * | 9/1998 | Haaga et al. ................ 600/425 |
| 5,878,746 A * | 3/1999 | Lemelson et al. .......... 600/407 |
| 5,915,038 A * | 6/1999 | Abdel-Mottaleb et al. .. 382/209 |
| 5,917,536 A * | 6/1999 | Kunimoto et al. .......... 347/247 |
| 6,115,489 A * | 9/2000 | Gupta et al. ................ 382/141 |
| 6,173,068 B1 * | 1/2001 | Prokoski ..................... 382/115 |
| 6,173,275 B1 * | 1/2001 | Caid et al. ..................... 706/14 |
| 6,175,658 B1 * | 1/2001 | Kump et al. ................. 382/266 |
| 6,473,517 B1 * | 10/2002 | Tyan et al. .................. 382/105 |
| 6,488,627 B1 * | 12/2002 | Kim ............................ 600/437 |
| 6,519,360 B1 * | 2/2003 | Tanaka ........................ 382/162 |
| 6,529,617 B1 * | 3/2003 | Prokoski ..................... 382/128 |
| 6,584,223 B1 * | 6/2003 | Shiiyama .................... 382/173 |
| 6,609,135 B1 * | 8/2003 | Omori et al. ............. 707/104.1 |

(Continued)

FOREIGN PATENT DOCUMENTS

EP        867830 A2 *  9/1998

(Continued)

OTHER PUBLICATIONS

Takahashi et al., "Development of Systems for Aiding Pathologic Diagnosis," Systems, Control and Information, vol. 41, No. 11, pp. 465-471, 1997 (15 pages).

*Primary Examiner*—Uyen-Chau N Le
(74) *Attorney, Agent, or Firm*—Sughrue Mion, PLLC

(57) ABSTRACT

A similar image search system includes an image database which stores a number of pieces of image data representing a number of images. Search image data representing the whole and/or a part of an image similar to which in feature is to be searched for is input and the image database is searched for similitude image data. A search report representing result of search is output.

31 Claims, 3 Drawing Sheets

U.S. PATENT DOCUMENTS

| | | |
|---|---|---|
| 6,691,134 B1 * | 2/2004 | Babula et al. ............ 707/104.1 |
| 6,730,032 B2 * | 5/2004 | Yamauchi ................... 600/443 |
| 6,771,263 B1 * | 8/2004 | Behrens et al. ............. 345/424 |
| 6,795,526 B2 * | 9/2004 | Kump et al. ................ 378/116 |
| 2001/0002934 A1 * | 6/2001 | Oosawa ...................... 382/130 |
| 2001/0010732 A1 * | 8/2001 | Oosawa ...................... 382/128 |
| 2001/0019623 A1 * | 9/2001 | Takeo ......................... 382/128 |
| 2002/0090132 A1 * | 7/2002 | Boncyk et al. ............. 382/154 |
| 2002/0106127 A1 * | 8/2002 | Kodama et al. ............ 382/195 |
| 2002/0168117 A1 * | 11/2002 | Lee et al. ................... 382/305 |
| 2002/0178135 A1 * | 11/2002 | Tanaka ......................... 707/1 |
| 2003/0013951 A1 * | 1/2003 | Stefanescu et al. ......... 600/407 |

FOREIGN PATENT DOCUMENTS

| | | |
|---|---|---|
| EP | 1092982 A1 * | 4/2001 |
| JP | 04129538 A * | 4/1992 |
| JP | 07237270 A * | 9/1995 |
| JP | 07271872 A * | 10/1995 |
| JP | 2001-325294 A | 11/2001 |
| JP | 2002-32476 | 1/2002 |
| JP | 2003271733 A * | 9/2003 |

* cited by examiner

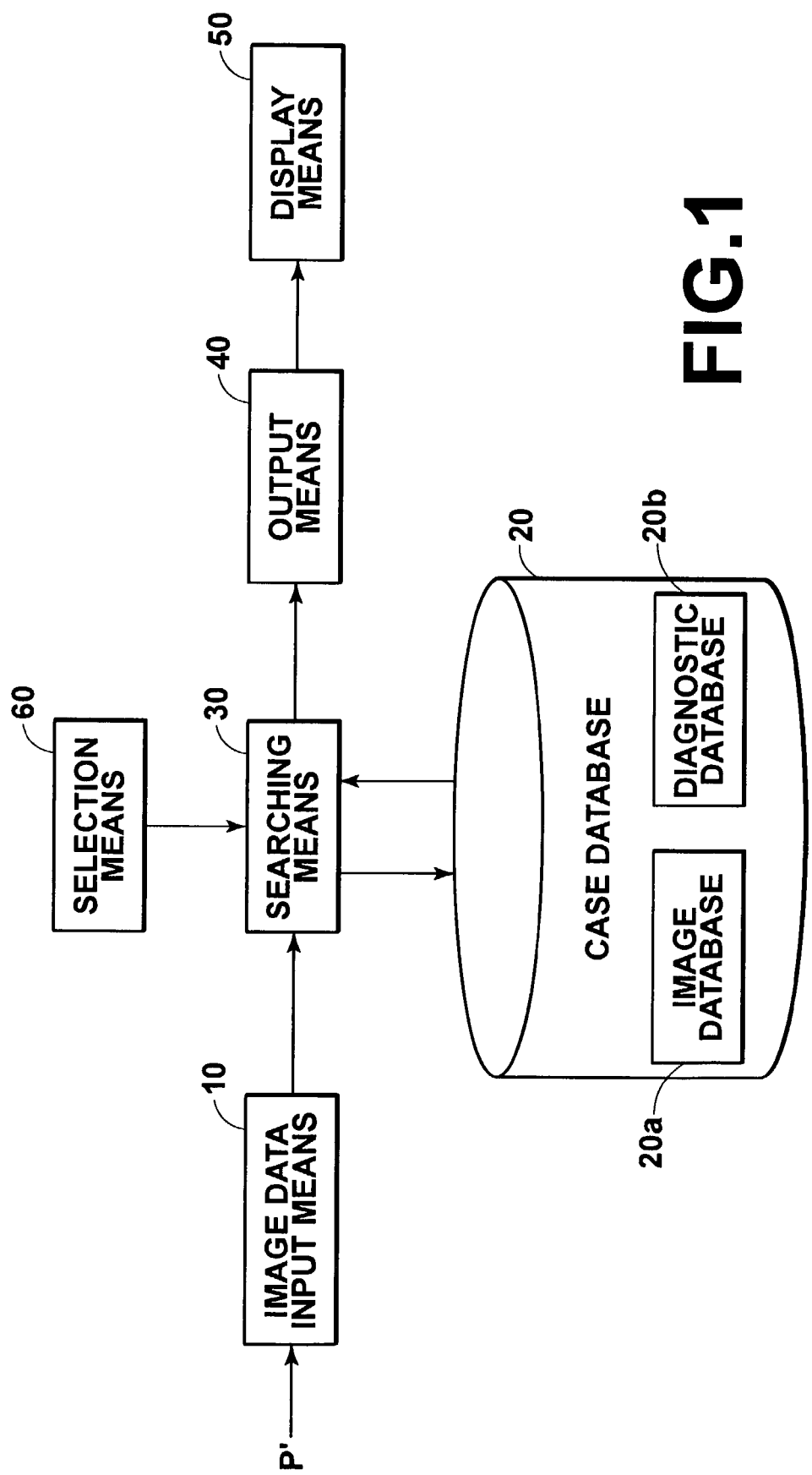

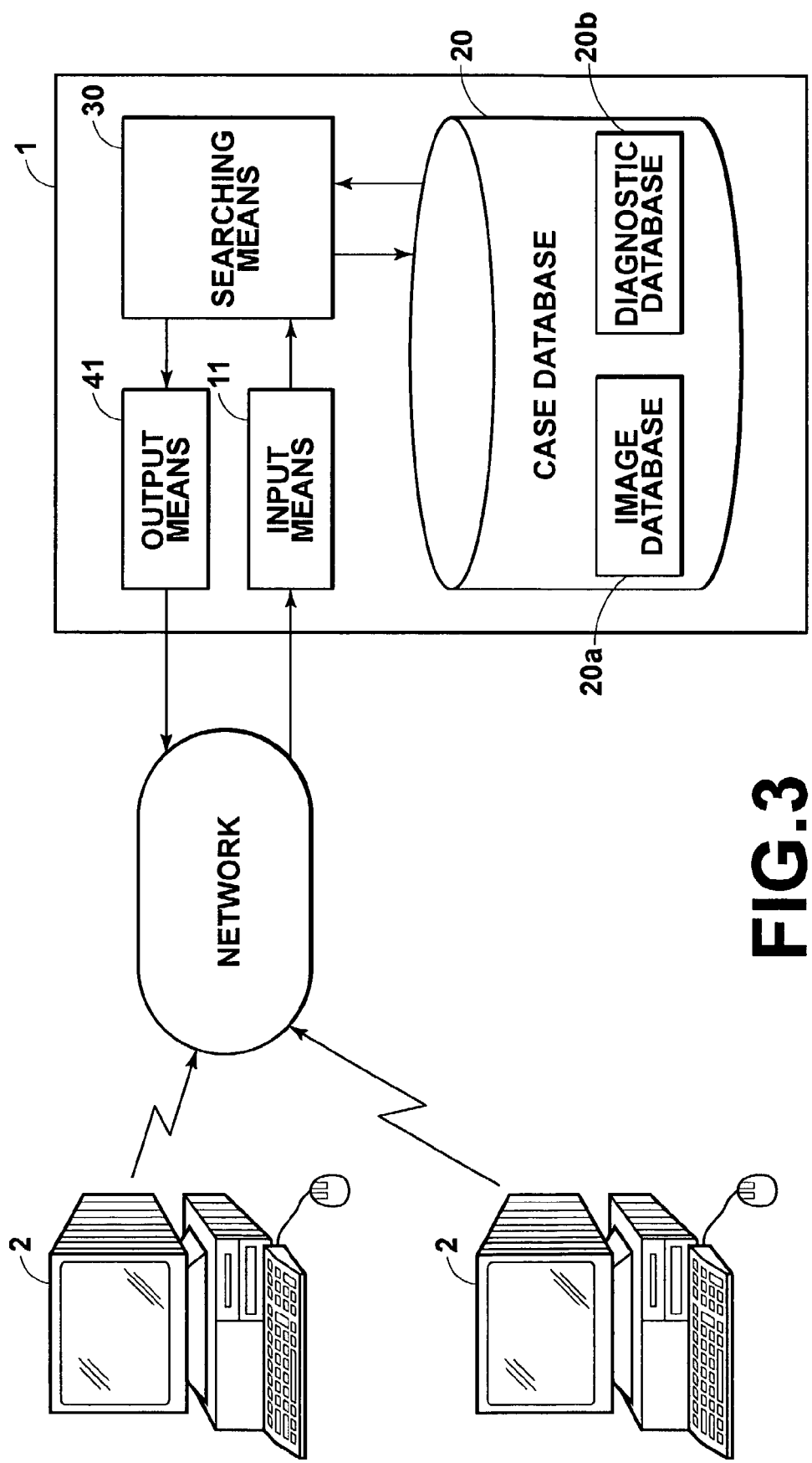

SIMILAR IMAGE SEARCH SYSTEM

BACKGROUND OF THE INVENTION

1. Field of the Invention

This invention relates to a similar image search system, and more particularly to a similar image search system for searching for an image similar to an image to be processed.

2. Description of the Related Art

There have been taken various medical images such as X-rays, computerized axial tomographies, and magnetic resonance images in various medical facilities. Generally these medical images are used for diagnosing and grasping the condition of the disease of the patient or progress of the disease and a reader such as a doctor diagnoses viewing an image and determines the course of treatment.

In medical facilities, the medical images used in diagnosis have been stored in the form of hard copies. However, in order to simplify the management of increasing medical images and to save the storing spaces, there has been proposed an image filing system in which pieces of digital image data are read out from medical images and the medical images are stored in recording media such as optical discs or magnetic discs in the form of image data.

Such a system can save the image storing spaces and makes it feasible to use images for various purposes.

In the case of an unexperienced reader or a rare disease or a disease out of reader's special interest, it is sometimes difficult for the reader to properly judge the name of the disease. In such a case, the reader sometimes consults other doctors or refers to past similar cases.

However it is very difficult to search for similar images among numerous images stored in the form of hard copies, and in the case of a small scale medical facilities storing a small amount of past cases, a desired similar case cannot be constantly obtained. Accordingly, there has been a demand for a system which makes it feasible to search for images similar to the image to be diagnosed (the image on the basis of which the patient's disease is to be diagnosed) among a number of images.

We, this applicant, has proposed a diagnosis-aid system in which information on prospective diseases are searched for and output on the basis of the condition of the disease input. (See Japanese Unexamined Patent Publication No. 2002-32476). In this system, when information on the condition of the patient such as result of reading an image of the affected part, result of diagnosis, result of interview with the patient, result of medical examination and the like is input, a name of disease prospected on the basis of the condition of the patient input or an image typical of the disease and the like are output, thereby aiding the doctor in making a proper diagnosis irrespective his or her experience or ability.

However, the diagnosis-aid system is arranged to input contents such as recorded in a medial chart and not to input an image to be diagnosed. That is, the diagnosis-aid system requires input of the reader's view and accordingly, is not effective when diagnosis of the image is difficult.

SUMMARY OF THE INVENTION

In view of the foregoing observations and description, the primary object of the present invention is to provide a similar image search system which can search for an image similar to the image to be diagnosed among a number of images.

In accordance with the present invention, there is provided a similar image search system comprising an image database which stores a number of pieces of image data representing a number of images, an image input means for inputting search image data representing the whole and/or a part of an image an image similar to which in feature is to be searched for (will be sometimes referred to simply as "object image data", hereinbelow), a searching means which searches the database for similitude image data representing an image which is similar to an image represented by the input search image data in feature (will be sometimes referred to simply as "similitude image data", hereinbelow), and a search report output means which outputs a search report representing result of search by the searching means.

The search report output by the search report output means may be a piece or pieces of similitude image data, if any, and may be a message representing the effect that there has been found no similitude image data when there has been found no similitude image data in the image database.

The searching means may judge whether a piece of image data is a similitude image data on the basis of one or more judgmental item. For example, the judgmental item may be shape, size, density pattern, position, direction, number and feature value of a shadow in the images represented by the two pieces image data to be compared, density pattern of the whole images represented by the two pieces image data to be compared, shape and/or size of structures (lung, heart and the like) in the whole images represented by the two pieces image data to be compared. The searching means may judge whether a piece of image data is a similitude image data on the basis of either one of such judgmental items or a combination of two or more of such judgmental items. The "feature value" is an index on the basis of which, for instance, the degree of malignancy of a detected abnormal shadow and in the case of a shadow of a tumor, the feature value includes, for instance, the degree of circularity, edge information on profile, a density histogram on an area, and the like (See, for instance, U.S. Pat. No. 5,732,121). The searching means may search the database by the use of either, the image data itself as a search key or various feature values extracted from the image data as a search key.

The similar image search system of the present invention may further comprise a selection means for selecting one or more judgmental items, and the searching means may judge whether a piece of image data is a similitude image data on the basis of the one or more judgmental items selected by the selection means.

The similar image search system of the present invention may further comprise a display means such as a CRT which displays the search report. Further, the display means may be connected by way of a network. That is, the image input means may be arranged to be able to receive input from a plurality of client terminals connected to the image input means by way of a network and the search report output means may be arranged to be able to output the search report to a plurality of client terminals by way of a network.

The "network" means an INTRANET in the hospital, internet, a leased line, and the like.

It is possible to arrange the image database to store a number of pieces of image data together with related information given thereto and the image input means to input an object image data together with related information while the searching means is arranged to search for a piece (a plurality of pieces) of similitude image data given related information equivalent to that of the object image data. That is, the searching means may be arranged to extract a piece (pieces) of image data representing an image similar to the image represented by the object image data and at the same time given equivalent related information.

The related information may be at least one of object part information representing the object part, modality information representing the modality of taking the image, personal information representing the name, age, sex and/or the like of the patient, and disease information representing the disease represented by the image.

For example, the object part information represents the object part of the image, chest, breast or so on, the modality information represents the modality of taking the image, CR, CT or so on. The personal information represents at least one of the name, age, sex, race, disease history, smoking history and/or the like of the patient. The disease information represents at least one name of disease obtained by diagnosis through the image, which may be the name of a prospective disease.

Further, it is possible to arrange the image database to store a number of pieces of image data together with position information representing the position of the object of the image represented by the image data, and the image input means to input an object image data together with position information representing a part on the basis of which similitude image data is to be searched for while the searching means is arranged to search for a piece (a plurality of pieces) of similitude image data taking into account the correspondence of position information.

The position information may represent either a position on the image or an anatomical position, which represents a part which can be anatomically defined such as "an upper portion of a right lung" or "a heart".

"To search for a piece (a plurality of pieces) of similitude image data taking into account the correspondence of position information" means to extract as similitude image data apiece (a plurality of pieces) of image data representing an image similar to the image represented by the object image data in the position equivalent to that represented by the input position information. The equivalent position may be a position which is anatomically equivalent but may be variously set, e.g., may be set as an area including an anatomically equivalent position.

The similar image search system of the present invention may further comprise a diagnostic database which stores pieces of diagnostic data related to the pieces of image data stored in the image database so that the searching means searches the diagnostic database for diagnostic data related to the extracted similitude image data and the search report output means outputs the extracted image data together with the diagnostic data related to the extracted similitude image data.

The "diagnostic data" means various pieces of information related to diagnosis such as result of diagnosis e.g., the name of the disease, the condition of progress of the disease, the course of treatment and/or examination, the name of the doctor in charge and/or the like.

The similar image search system of the present invention may further comprise an addition storage means which adds the object image data input through the image input means to the image data stored in the image database.

In accordance with the similar image search system of the present invention, a piece of similitude image data can be properly extracted from a number of pieces of image data.

When the searching means judges whether a piece of image data is a similitude image data on the basis of two or more judgmental items, a piece of similitude image data can be extracted on the basis of a plurality of judgmental items and more detailed search can be realized. For example, in the case of a tumor which is a form unique to cancer, feature values on shape and edges of the tumor are indexes of the degree of malignancy. Accordingly, when feature values on shape and edges of tumor are included in the judgmental items, similitude image data can be extracted more properly than when similitude image data is searched for on the basis of a single feature value.

When the similar image search system of the present invention further comprises a selection means for selecting one or more judgmental items, the judgmental items can be changed according to the purpose of diagnosis and/or the kind of shadow, and accordingly, various pieces of image data can be referred to from a plurality of viewpoints, whereby more effective information can be obtained.

When the image input means is arranged to be able to receive input from a plurality of client terminals connected to the image input means by way of a network and the search report output means is arranged to be able to output the search report to a plurality of client terminals by way of a network, even small-scale medical facilities which cannot be equipped with an image database storing therein a number of pieces of image data can search for similitude image data among a number of pieces of image data by only purchasing a client terminal, which is economically advantageous.

When the image database stores a number of pieces of image data together with related information given thereto and the image input means inputs an object image data together with related information while the searching means is arranged to search for a piece (a plurality of pieces) of similitude image data given related information equivalent to that of the object image data, the similitude image data can be searched for not simply on the basis of resemblance of images but taking into account various pieces of information and accordingly, similitude image data representing an image more similar to the image represented by the object image data can be extracted.

For example, when the related information represents the modality of taking the image, the similitude image data can be searched for among those in similar image conditions, and accordingly, similitude image data can be more accurately extracted. Further when the related information is personal information on the patient, the similitude image data can be searched for among those whose objects are physiologically similar to the object of the input image data, more effective information can be obtained when the disease depends upon the age and/or sex of the patient. Further when the related information is disease information, more effective information can be obtained when prospective disease can be limited.

Further, when the similitude image data is searched for taking into account the correspondence of position information, similitude image data which is clinically more meaningful can be obtained since disease is related to anatomical structure.

Further, when the search report output means outputs the extracted image data together with the diagnostic data related to the extracted similitude image data, more effective information can be obtained when the reader wavers in his or her judgment.

Further, when the similar image search system of the present invention further comprises an addition storage means which adds the object image data input through the image input means to the image data stored in the image database, the image database can be reinforced to be able to provide more effective information.

BRIEF DESCRIPTION OF THE DRAWINGS

FIG. 1 is a view showing a similar image search system in accordance with an embodiment of the present invention, FIG. 3 is a view showing a similar image search system in accordance with another embodiment of the present invention.

DESCRIPTION OF THE PREFERRED EMBODIMENTS

Figure 2A:
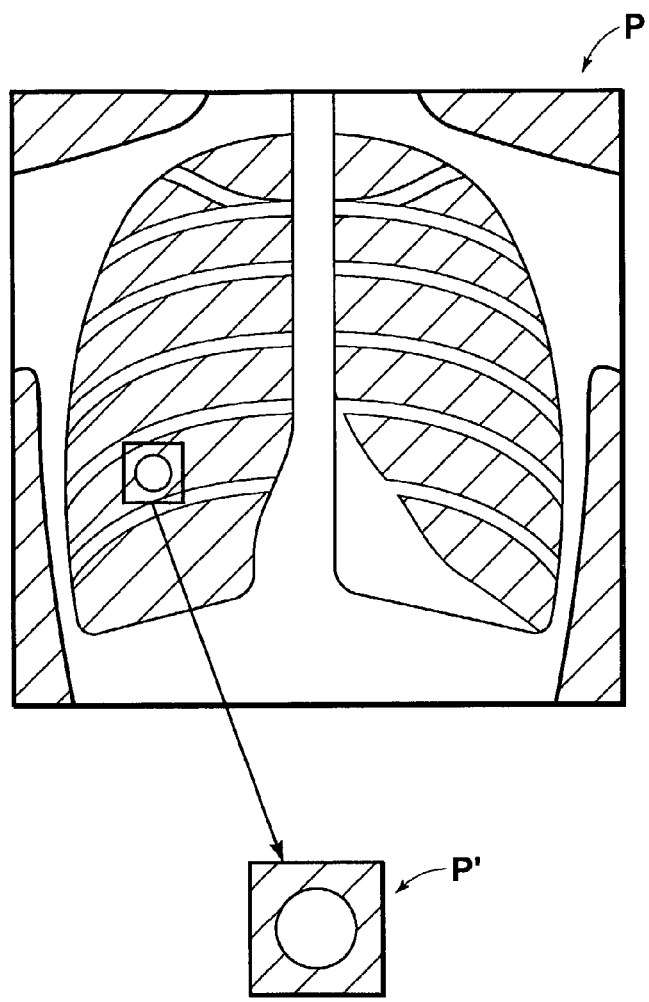
FIGS. 2A and 2B are views respectively showing examples of an image on the basis of which similitude image data is to be searched and a search report to be displayed.

In FIG. 1, a similar image search system in accordance with an embodiment of the present invention comprises an image data input means 10 which inputs ROI image data (search image data) P' representing a region of interest (ROI) set in an image, a case database 20 which stores a number of pieces of image data representing a number of images and pieces of diagnostic data related to diagnosis, a searching means 30 which searches the case database 20 for similitude image data representing an image which is similar to the image represented by the input ROI image data P' in feature, a selection means 60 for selecting one or more judgmental items on the basis of which the searching means 30 judges whether a piece of image data is a similitude image data, an output means 40 which outputs a search report representing result of search by the searching means 30, and a display means 50 which displays on its screen the search report output by the output means 40.

The case database 20 comprises an image database 20*a* which stores a number of pieces of image data representing a number of images and a diagnostic database 20*b* which stores pieces of diagnostic data related to the pieces of image data stored in the image database 20*a*. In the image database 20*a*, a number of image data representing images of various objects diagnosed in the past are stored, and in the diagnostic database 20*b*, pieces of diagnostic data related to the pieces of image data stored in the image database 20*a* are stored related with the pieces of image data. As the diagnostic data, various pieces of data on diagnosis such as the name of disease, measures (course of treatment and/or examination), and the like are stored in the diagnostic database 20*b*.

The selection means 60 is for selecting judgmental items on the basis of which whether a piece of image data is a similitude image data is determined. For example, the selection means 60 may be in the form of a menu and the reader (will be sometimes referred to as "the operator", hereinbelow) selects desired judgmental items, whereby judgmental items are set. In this particular embodiment, judgmental items are selected from shape, size, direction and density pattern of a shadow in the ROI image.

The searching means 30 judges whether a piece of image data is a similitude image data on the basis of the judgmental items selected by the selection means 60. In this particular embodiment, the searching means 30 extracts only a piece of similitude image data.

FIG. 2A shows a radiation image P of a chest and a ROI image P', a region of interest in the radiation image P. (Image data and the image represented by the image data will be described on the basis of the same reference number for the purpose of simplicity, hereinbelow.) A circular shadow which is a suspected tumor shadow exists in the right lung in the radiation image P. The ROI image P' is extracted by a reader (doctor), is high in brightness all over and includes the isolated circular shadow. The ROI image P' is designated by the use of a position designation means such as a mouse.

Operation of the similar image search system of this embodiment will be described, hereinbelow.

The operator designates the position and the range of a suspected diseased part on a image P of a chest displayed on a screen and clicks on a similar image data search button on the screen. By this action, ROI image data P' is input by the image data input means 10.

Though the judgmental item has been set to some of the items, the judgmental item can be changed by the selection means 60. That is, when a judgmental item change button provided in the screen is clicked, a judgmental item selection menu appears on the screen. The operator can select one or more items from the judgment items displayed in the menu. When the operator selects, for instance, "shape of shadow", information representing that whether a piece of image data is a similitude image data is to be judged on the basis of shape of the shadow is input into the searching means 30 and the judgmental item is changed so.

When the image data input means 10 inputs the ROI image data P', the searching means 30 searches the image database 20*a* for a piece of similitude image data having a part similar to the input ROI image data p' on the basis of the selected judgmental item. The searching means 30 searches the diagnostic database 20*b* for the diagnostic data related to the extracted image data.

Since "shape of the shadow" has been selected as the judgmental item, the searching means 30 searches similitude image data on the basis of the circular shadow included in the ROI image P'. That is, the searching means searches similitude image data among the pieces of image data representing a chest having a circular shadow and extracts a piece of image data which is the highest in consistency as the similitude image data.

The similitude image data extracted by the searching means 30 is output to the display means 50 by the output means 40. FIG. 2A shows an example of the search report to be displayed by the display means 50. As shown in FIG. 2A, the similitude image having a circular diseased part is displayed together with result of diagnosis (the name of disease: early stage lung cancer, measures: close examination by CT).

As can be understood from the description above, in the similar image search system of this embodiment, since the similitude image data is displayed together with the diagnostic data related to the extracted similitude image data, information effective as diagnostic aid when the reader wavers in his or her judgment can be obtained.

Though, in the embodiment described above, only a piece of similitude image data is extracted, two or more pieces of image data may be extracted. For example, a desired number (e.g., 3 or 20) of pieces of similitude image data extracted in the order of similarity may be displayed or pieces of image data higher than a predetermined reference (e.g., when similarity can be quantized, the predetermined reference may be set to 80%) may be all displayed. With this arrangement, the doctor or the like can select an image more conforming to the case to be diagnosed among a plurality of similar cases. That is, even an experienced doctor cannot be completely free from oversight, and accordingly, by aiding the doctor in diagnosis by listing several suspected cases, more accurate diagnosis can be realized. The "similarity" may be a ratio of sizes when the judgmental item is "size of shadow" or the degree of overlap after enlargement/reduction (e.g., the ratio of area of the overlapped part to area of the whole) when the judgmental item is "shape of shadow". The similarity may be variously set for other judgmental items.

similitude image data may be searched for on the basis of whole image data representing the whole image in place of the ROI image data. This form of the similar image search system of the present invention is advantageous when a similar case of disease represented by the whole image is to be searched for. For example, this form can be employed when a similar case of disease where the whole lung is whitened or an organ is deformed. In this case, for instance, "density pattern of the whole image" can be employed as the judgmental item. Further, the ROI image data and the whole image data may be both input. In this case, similitude image data similar to the input image data in properties of shadow can be searched for on the basis of the ROI image data and can be searched for with the position of the ROI or the properties of the part around the ROI set as the judgmental item on the basis of the whole image data.

When the similitude image data is searched for on the basis of the whole image data, the whole processing from inputting image data to outputting similitude image data can be automated since it is not necessary for the operator to designate the ROI. By arranging the system to automatically set the ROI on the basis of the image data, the whole processing from inputting image data to outputting similitude image data can be automated even when the similitude image data is to be searched for on the basis of the ROI image data.

The similar image search system of the present invention may be arranged so that feature values of the abnormal shadow included in the ROI image are calculated and the similitude image data is searched for with the feature values employed as the judgmental item. That is, image data is input, an abnormal shadow is detected and feature values thereof are calculated on the basis of the image data, and the similitude image data similar to the object image data in the feature values and the kind of the abnormal shadow may be extracted. In this case, it is preferred that since result of detection of the abnormal shadow in image data stored in the image database and result of calculation of the feature values are necessary in search, these pieces of data have been stored in the diagnostic database 20b as diagnostic data related to the similitude image data.

A similar image search system in accordance with another embodiment of the present invention will be described with reference to FIG. 3, hereinbelow. In this embodiment, the elements analogous to those in the embodiment described above are given the same reference numerals and will not be described here.

The similar image search system (server) 1 in accordance with this embodiment comprises an input means 11 which are connected to a plurality of client terminals 2 by way of a network so that object image data and/or judgmental items can be input into the input means through each of the client terminals 2, a case database 20 which stores a number of pieces of image data representing a number of images and pieces of diagnostic data related to diagnosis, a searching means 30 which searches the case database 20 for similitude image data representing an image which is similar to the image represented by the input image data in feature, an output means 41 which outputs a search report representing result of search (the extracted similitude image data and the diagnostic date related thereto) by the searching means 30 to the client terminals 2 connected thereto by way of the network 3.

The client terminals 2 are installed at places remote from the server 1. In this particular embodiment, it is assumed that the server 1 is installed in a large-scale hospital and the client terminals 2 are respectively installed in a plurality of small-scale hospitals in association with the large-scale hospital. The server 1 and the client terminals 2 may be variously installed. For example, the server 1 is installed in a data center with a plurality of client terminals 2 installed in a medial facility.

The input means 11 comprises an image data input means which inputs object image data and information input means which inputs judgmental items. The judgmental items are selected by the operator in the judgmental item menu displayed on the screen of the client terminal 2. Otherwise, different judgmental items may be set in advance by the client terminals 2, and the input means may input information representing the judgmental items set in the client terminal in advance together with object image data.

Operation of the similar image search system of this embodiment will be described, hereinbelow.

The operator designates the position and the range of a suspected diseased part on a image P of a chest displayed on a screen of the client terminal 2 and selects a desired judgmental item ("shape of shadow" in this particular embodiment). Then when the operator clicks on a similar image data search button on the screen, ROI image data P' and information representing the selected judgmental item are input into the server 1 through the input means 11.

When the ROI image data P' and the information representing the selected judgmental item are input into the server 1, the searching means 30 searches the image database 20a for a piece of similitude image data having a part similar to the input ROI image data p' on the basis of the selected judgmental item. The searching means 30 searches the diagnostic database 20b for the diagnostic data related to the extracted image data.

The similitude image data extracted by the searching means 30 is output to the client terminal 2 by way of the network 3 by the output means 41 and displayed on the screen of the client terminal 2.

As can be understood from the description above, in the similar image search system of this embodiment, since the similitude image data can be searched for from a plurality of client terminals connected thereto by way of a network, even small-scale medical facilities can refer to a number of pieces of image data. Further, the judgmental item can be selected from the client terminals 2, similitude image data conforming to the purpose of diagnosis can be referred.

Further, it is possible to provide the server 1 with a search information recording means which records, for instance, the number of times of search and/or the amount of data transferred between the server 1 and the client terminal 2 so that accounting information can be calculated on the server 1, which makes it feasible for the server 1 to manage the client terminals 2.

Figure 2B:
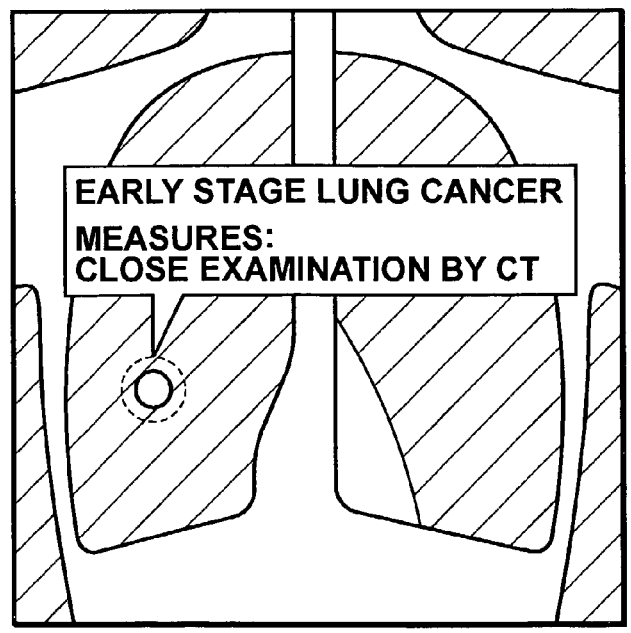

As the search report to be displayed by the display means 50 or the client terminals 2 need not be limited to that shown in FIG. 2B. For example, the whole image represented by the similitude image data and the partial image representing a similar part may be displayed in a screen, a similitude image data may be displayed together with the similarity, or pieces of similitude image data may be classified into a plurality of categories and the case most similar to the object image data in each category may be displayed as the similitude image data. The similarity may be displayed, for instance, in the form of values, in the form of size of a frame circumscribing the partial image, or in the form of thickness of a frame circumscribing the partial image. The system may be arranged to display no image when the similarity of the most similar image data is not higher than a predetermined reference level (e.g., 20%). Further, when there cannot be found a piece of similitude image data, a message representing that there cannot be found a similar case may be displayed. The categories according to which the pieces of similitude image data is classified may be, for instance, the condition of the abnormal shadow (e.g., malignant, benignant or normal). That is, when pieces of similitude image data are not classified by categories, only malignant cases are sometimes displayed. However, when pieces of similitude image data are classified by categories, apiece of similitude image data can be displayed for each of the malignant case, the benignant case and the normal case, which results in more accurate diagnosis.

Further, in the embodiments described above, the searching means 30 may search for the similitude image data further on the basis of information other than image data. For example, related information such as on the object part, the modality of taking the image, the patient, and the disease represented by the image is stored in the diagnostic data as the diagnostic data, and the searching means is arranged to search for a piece (a plurality of pieces) of similitude image data taking into account these pieces of information. In this case, a designating means for designating the related information is further provided and the related information designated by the designating means is input together with the object image data (ROI image data) by the image data input means 10 or the input means 11. The designating means may manually input the item and the content thereof (e.g., that the object is a chest) by the use of an input means such as a keyboard and/or a mouse, may input only the item of the related information (in the case where the contents of each piece of information are recorded in advance in a predetermined recording means in relation to the object image data).

For example, information representing that the object part is a chest is input by the image data input means 10 or the input means 11 together with the object image data (ROI image data), the searching means 30 searches the image data base 20a for pieces of image data whose object part is a chest and extracts as the similitude image data a piece or pieces of image data which has a part similar in feature to the object image data from the pieces of image data whose object part is a chest.

Further, when information representing that the suspected disease is, for instance, breast cancer or fibromatosis is input through the image data input means 10 or the input means 11 together with object image data (ROI image data), the searching means 30 searches the image data base 20a for pieces of image data whose disease information is breast cancer or fibromatosis and extracts as the similitude image data a piece or pieces of image data which has a part similar in feature to the object image data from the pieces of image data whose disease information is breast cancer or fibromatosis. When the name of disease is not designated, all the pieces of image data similar to the object image data whose object parts are not limited and include a normal part are extracted.

The designated related information need not be limited to one piece of information. For example, a plurality of pieces of related information, for instance, one representing that the object part is a chest and another representing that the modality of taking the image is CR may be designated. The personal information represents the name, age, sex, race, disease history, smoking history and/or the like of the patient. The similitude image data may be searched for on the basis of a combination of at least one of these pieces of personal information and other related information (e.g., the disease information).

When symptom data is included in the diagnostic data stored in the diagnostic database 20b, the similitude image data which is similar to the object image data in both feature and symptom can be obtained by the use of the symptom data, whereby a more similar case can be extracted.

Further, the searching means 30 may be arranged to extract from the image database 20a as the similitude image data a piece (or pieces of) image data which is similar to the object image data in equivalent anatomic position.

For example, a position designating means which inputs the anatomical position (e.g., right lung) by the use of, for instance, a keyboard is provided and the image data input means 10 or the input means is arranged to input the designated anatomical position together with the object image data. The searching means 30 is arranged to extract from the image database 20a as the similitude image data a piece (or pieces of) image data which is similar to the object image data in equivalent anatomic position on the basis of the designated anatomical position.

When the object image data is a ROI image data representing a part of the image of an object, the similar image sear system of the present invention may be provided with an automatic position identifying means which automatically identifies the position of the ROI (may be either the position on the image represented by, for instance, coordinates or an anatomical position) so that a piece of image data which is similar to the object image data in feature in the equivalent position is extracted on the basis of the position identified by the automatic position identifying means.

It is possible to provide the client terminals connected to the server by way of a network with an addition storage means so that diagnosed image data can be added to the image database 20a. The addition storage means may be directly provided on the similar image search system without network. It is preferred that the addition storage means automatically stores predetermined information in the image database 20a or the diagnostic database on the basis of a report or an electronic medical chart which a doctor or the like creates after reading an image or after making diagnosis. Further it is possible to provide a user database in addition to the image data base 20a and to store diagnosed cases in the user database by medical facilities. For example, it is possible to install the image database in a data center and the user database in each medical facility. In this case, it is possible to designate the database to be searched or to cause the searching means to search all the databases. By providing a means for additionally storing diagnosed image data to the similar image search system of the present invention, the similitude image data can be searched for among larger number of cases and accordingly, the system can offer information more useful for diagnosis.

What is claimed is:

1. A similar image search system comprising:
   an image database which stores a number of pieces of image data representing a number of images,
   an image input means for inputting search image data representing a whole and/or a part of an image similar to which in feature is to be searched for,
   a searching means which searches the database for similitude image data representing an image which is similar to an image represented by the input search image data in feature, wherein the similitude level for the search is 20%,
a search report output means which outputs a search report representing result of search by the searching means, and
a diagnostic database which stores pieces of diagnostic data related to the pieces of image data stored in the image database so that the searching means searches the diagnostic database for diagnostic data related to the extracted similitude image data and the search report output means outputs the extracted image data together with the diagnostic data related to the extracted similitude image data,
wherein the diagnostic data related to the extracted similitude image data includes a name of disease.

2. A similar image search system as defined in claim 1 in which the searching means judges whether a piece of image data is a similitude image data on the basis of one or more judgmental item.

3. A similar image search system as defined in claim 2 further comprising a selection means for selecting one or more judgmental items, wherein the searching means judges whether a piece of image data is a similitude image data on the basis of the one or more judgmental items selected by the selection means.

4. A similar image search system as defined in claim 3, wherein the selection means selects one or more judgmental items from a plurality of judgmental items.

5. A similar image search system as defined in claim 4, wherein the plurality of judgmental items include at least one of a shape of a shadow, a size of a shadow, a direction of a shadow, and a density pattern of a shadow in the search image data.

6. A similar image search system as defined in claim 4, wherein the plurality of judgmental items are displayed in a displayed judgmental menu.

7. A similar image search system as defined in claim 4, wherein the plurality of judgmental items include at least one of a shape of a shadow, a direction of a shadow and a density pattern of a shadow in the search image data.

8. A similar image search system as defined in claim 2, wherein the selection means is a menu.

9. A similar image search system as defined in claim 2, wherein the search report comprises a plurality of images.

10. A similar image search system as defined in claim 1 in which the image input means is arranged to receive input from a plurality of client terminals connected to the image input means by way of a network, and the search report output means is arranged to be able to output the search report to a plurality of client terminals by way of a network.

11. A similar image search system as defined in claim 10 further comprising a selection means for selecting one or more judgmental items from a plurality of judgmental items, wherein the searching means judges whether a piece of image data is a similitude image data on the basis of the one or more judgmental items selected by the selection means and the plurality of judgmental items are displayed in a judgmental menu displayed in a client terminal of the plurality of client terminals.

12. A similar image search system as defined in claim 10, wherein the search report output means is in a data center and the client terminals are in medical facilities.

13. A similar image search system as defined in claim 1 in which the image database stores a number of pieces of image data together with related information given thereto and
the image input means inputs an object image data together with related information while the searching means is arranged to search for a piece or a plurality of pieces of similitude image data given related information equivalent to that of the object image data.

14. A similar image search system as defined in claim 13 in which the related information is at least one of object part information, modality information, personal information, and disease information.

15. A similar image search system as defined in claim 1 in which the image database stores a number of pieces of image data together with position information representing the position of the object of the image represented by the image data, and
the image input means inputs an object image data together with position information representing a part on the basis of which similitude image data is to be searched for, and
the searching means is arranged to search for a piece or a plurality of pieces of similitude image data taking into account the correspondence of position information.

16. A similar image search system as defined in claim 1 further comprising an addition storage means which adds the object image data input through the image input means to the image data stored in the image database.

17. A similar image search system as defined in claim 16, wherein the image data after diagnosis is additionally stored in the database.

18. A similar image search system as defined in claim 1 further comprising a diagnostic database which stores pieces of diagnostic data related to the pieces of image data stored in the image database.

19. A similar image search system as defined in claim 18, wherein the search report comprises similitude image data and diagnostic data related to the similitude image data.

20. A similar image search system as defined in claim 1, wherein the search report includes the searched similitude image data.

21. A similar image search system as defined in claim 1, wherein the image includes at least one of an X-ray image and a computed tomography (CT) image.

22. A similar image search system as defined in claim 1, wherein the image is an image of an anatomical structure of a subject.

23. A similar image search system as defined in claim 1, wherein the similitude image data representing the image is similar to the image represented by the input search image data in feature according to a predetermined reference level.

24. A similar image search system as defined in claim 1, wherein the similitude image data representing the image is similar to the image represented by the input search image data in feature when a similarity between the similitude image data representing the image and the image represented by the input search image data is higher than a predetermined reference level.

25. A similar image system as defined in claim 1, wherein the image is an image of an anatomical structure of a subject.

26. A similar image system as defined in claim 1, wherein the search image data is a graphical image.

27. A similar image search system as defined in claim 1, wherein the search image data is a region of interest (ROI) image data, the ROI image data is designated on an input radiation image data, and the searching means searches the database for the similitude image data having a part similar to the ROI image data.

28. A similar image search system of claim 1, wherein the search image data is a region of interest (ROI) image data, the similitude image data similar to the search image data in properties of shadow is searched for based on the ROI image data and with a position of the ROI or properties of a part around the ROI set as a judgmental item on the basis of the whole image data.

29. A similar image search system of claim 1, wherein the search image data is a region of interest (ROI) image data and the ROI image data is automatically set based on the image data.

30. A similar image search system of claim 1, wherein the search image data is a region of interest (ROI) image data, feature values of an abnormal shadow included in the ROI image data are calculated and the similitude image data is searched for with the feature values as a judgmental item.

31. A similar image search system comprising:
an image database which stores a number of pieces of image data representing a number of images,
an image input means for inputting search image data representing a whole and/or a part of an image similar to which in feature is to be searched for,
a searching means which searches the database for similitude image data representing an image which is similar to an image represented by the input search image data in feature, and
a search report output means which outputs a search report representing result of search by the searching means,
wherein the similitude image data representing the image is similar to the image represented by the input search image data in feature when a similarity between the similitude image data representing the image and the image represented by the input search image data is higher than a predetermined reference level, and
wherein the predetermined reference level is 20%.

* * * * *